US009035844B2

(12) United States Patent
Malewicki et al.

(10) Patent No.: US 9,035,844 B2
(45) Date of Patent: May 19, 2015

(54) TELEMETRY EXTENSION CABLE

(71) Applicant: Medtronic, Inc., Minneapolis, MN (US)

(72) Inventors: Kathleen R. Malewicki, Beverly, MA (US); David A. Casavant, Reading, MA (US); Edward D. Goff, Mahtomedi, MN (US); Gary H. Kemmetmueller, Coon Rapids, MN (US); David J. Peichel, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/896,494

(22) Filed: May 17, 2013

(65) Prior Publication Data

US 2014/0340272 A1 Nov. 20, 2014

(51) Int. Cl.
*H01Q 7/06* (2006.01)
*H01Q 7/00* (2006.01)
*A61N 1/372* (2006.01)

(52) U.S. Cl.
CPC . *H01Q 7/06* (2013.01); *H01Q 7/00* (2013.01); *A61N 1/37223* (2013.01); *A61N 1/37229* (2013.01); *A61N 2001/37294* (2013.01)

(58) Field of Classification Search
CPC . A61N 1/37252; A61N 1/37223; A61N 1/08; A61N 1/3727; A61N 1/37211; A61N 1/37247
USPC ............... 343/788, 718, 867; 607/60; 455/73
See application file for complete search history.

(56) References Cited

U.S. PATENT DOCUMENTS 3,657,652 A * 4/1972 Smith ........................... 343/709
5,383,915 A * 1/1995 Adams ............................ 607/60
5,759,199 A 6/1998 Snell et al.
6,201,993 B1 3/2001 Kruse et al.
6,224,617 B1 * 5/2001 Saadat et al. .................. 606/170
6,463,329 B1 * 10/2002 Goedeke ......................... 607/60
6,895,281 B1 5/2005 Amundson et al.
6,930,602 B2 8/2005 Villaseca et al.
7,010,355 B2 3/2006 Lee
7,092,761 B1 8/2006 Cappa et al.
7,103,414 B1 9/2006 Poore et al.
8,214,045 B2 7/2012 Kronich et al.
8,437,855 B2 * 5/2013 Sjostedt et al. ................. 607/37
2002/0082665 A1 6/2002 Haller et al.
2003/0171789 A1 * 9/2003 Malek et al. ..................... 607/60
2008/0127478 A1 6/2008 Phillips et al.

(Continued)

FOREIGN PATENT DOCUMENTS

EP        2314215 A2     4/2011
WO      01/87413 A1    11/2001
WO   2009/058788 A2     5/2009

OTHER PUBLICATIONS (PCT/US2014/026943) PCT Notification of Transmittal of the International Search Report and the Written Opinion of the International Searching Authority, Mailed Aug. 6, 2014, 9 pages.

*Primary Examiner* — Robert Karacsony

(57) ABSTRACT

The invention of the disclosure is an extension cable to connect via telemetry, an external medical device in a non-sterile zone with a medical device that is within a sterile zone. The telemetry extension cable includes a cable having a length and comprising a conductor, a first RF antenna attached at one end of the cable and a second RF antenna attached at a second end of the cable, at least one of the first or second antennas configured to transmit and receive RF signals to and from an implantable medical device.

7 Claims, 3 Drawing Sheets

(56) References Cited

U.S. PATENT DOCUMENTS

| | | |
|---|---|---|
| 2009/0112626 A1 | 4/2009 | Talbot et al. |
| 2009/0228074 A1* | 9/2009 | Edgell et al. .................. 607/60 |
| 2010/0117454 A1* | 5/2010 | Cook et al. .................. 307/104 |
| 2011/0043051 A1* | 2/2011 | Meskens .................. 307/104 |
| 2011/0245886 A1* | 10/2011 | Stetson et al. .................. 607/2 |
| 2011/0245892 A1 | 10/2011 | Kast et al. |
| 2011/0313486 A1 | 12/2011 | Castro et al. |
| 2012/0203317 A1* | 8/2012 | Valentine et al. ............. 607/116 |

* cited by examiner

TELEMETRY EXTENSION CABLE

FIELD

The present disclosure is related to cable for transmitting radio frequency (RF) signals to and from an implantable or other medical device to a medical device programmer or similar device.

BACKGROUND

Some implantable medical devices require the placement of a telemetry head in close proximity to the device in order for the device to communicate with an external medical device such as a programmer. During implantation of such an implantable medical device, physicians may wish to test or program the device while in a sterile environment such as an operating room. In such cases, the telemetry head and the programmer would be required to be sterilized prior to use.

SUMMARY

In one aspect, the invention of the disclosure is an extension cable to connect via telemetry, an external medical device in a non-sterile zone with a medical device that is within a sterile zone.

In one embodiment, the telemetry extension cable comprises or consists essentially a cable having a length and comprising a conductor, a first RF antenna attached at one end of the cable and a second RF antenna attached at a second end of the cable, at least one of the first or second antennas configured to transmit and receive RF signals to and from an implantable medical device.

In other embodiments, cable portions are connected together at a point between the first and second antennas via cable connectors that releasably connect the cable portions together.

In another aspect, the invention of the disclosure is a system for connecting an external medical device to an implantable medical device. The system comprises a telemetry extension cable of the disclosure and an external medical device having a telemetry head connected to the external medical device.

In another aspect, the invention of the discourse is a kit which includes a cable having a first portion with a first length and a second portion with a second length, the first portion of the cable having an RF antenna at an end and a cable connector at another end, the second portion of the cable having an RF antenna on an end and a cable connector at another end, the cable connectors configured to releasably connect the first and second cable portions together, at least one of the first or second cable portions is sterile.

In other embodiments, at least the sterile portion of the cable is packaged within sterile packaging.

In another aspect, the invention of the disclosure provides a method of connecting via wired telemetry a non-sterile medical device with a medical device located within a sterile zone by utilizing a telemetry extension cable described in this disclosure.

DETAILED DESCRIPTION

In this disclosure an antenna is a specialized transducer that converts radio-frequency (RF) fields into alternating current (AC) or vice-versa.

The telemetry extension cables of the disclosure are useful for communication with a medical device just prior to complete implantation within a patient. Certain implantable medical devices communicate with a medical device programmer by placing a programmer telemetry head in close proximity to the implanted medical device. According to current practice, if before closing the incision, a physician wishes to test the implanted device before closing the incision, the programmer telemetry head would need to be sterile. In such situations, a telemetry extension cable of the disclosure could be used to connect in a telemetric sense a programmer's telemetry head that is situated outside of the sterile environment with the partially implanted medical device.

In such a configuration, one of the RF antennas would be placed under the telemetry head and the other RF antenna at the other end of the extension cable would be placed in close proximity to the incision and partially implanted medical device. In this situation, both RF antennas and the cable of the telemetry extension cable would be packaged in a sterile package with one end of the telemetry extension cable would remain sterile and the other end of the telemetry extension cable would be placed into the non-sterile environment or zone and the RF antenna would be placed under the medical device programmer head.

In some embodiments, the telemetry extension cable could be manufactured using materials to allow for re-sterilization or of the telemetry extension cable or it could be manufactured using less expensive materials for disposable use. In another embodiment, a telemetry extension cable of the disclosure could be configured with a suitable in-line, dis-connectable and re-connectable cable connector along the length of the cable and between the RF antennas, for example, about 0.5 m from the RF antenna under the medical device programmer telemetry head. Such an arrangement would allow that a portion of the cable and the RF antenna in close proximity to the implanted device would only be required to be sterile, while the other portion of the cable and the RF antenna communication with a telemetry head could be outside of the sterile zone. In this configuration, only part of the telemetry cable could be disposable and the non-sterile portion of the telemetry extension cable could be re-used. In other embodiments, the telemetry extension cables described in this disclosure can also incorporate a magnet, for example, a low profile magnet, in the RF antenna that would be placed near and implantable medical device.

Figure 1:
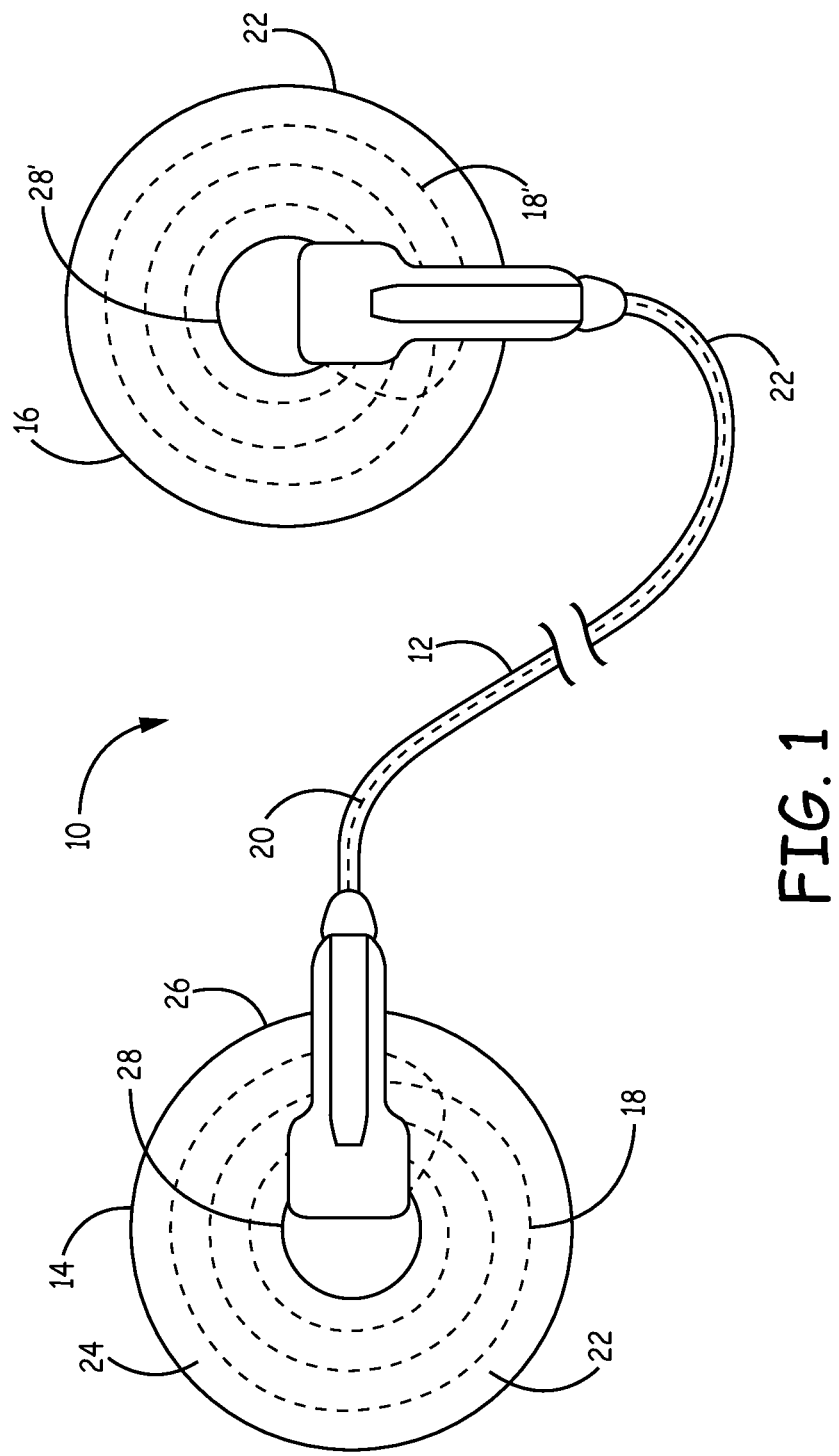
FIG. 1 is a depiction of an embodiment of a telemetry extension cable of the disclosure.

An embodiment of a telemetry extension cable of the disclosure is shown in FIG. 1. Telemetry extension cable 10 includes a cable 12 comprising a conductor 20 having a length. Attached at each end of the cable 12 is a first RF antenna 14 and a second RF antenna 16. In this embodiment, each of the antennas 14, 16 contain a conductor in the form of a coil 18, 18' and each antenna is in the form of or has a shape of a substantially planar disc having a top planar side 24 and a bottom planar side 26 defined by a hole 28, 28'. In this embodiment, the cable 12 and the antennas 18, 18' are coated in a polymer coating 22.

Figure 2:
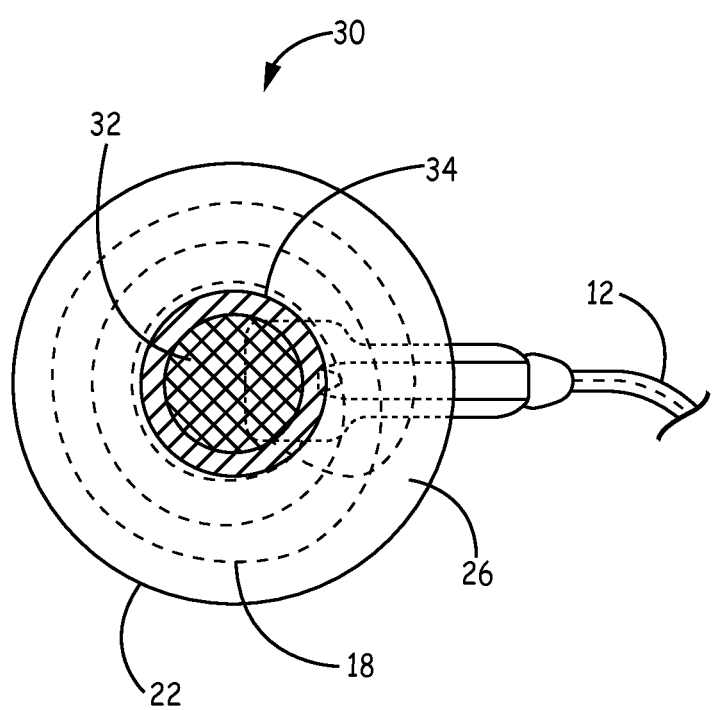
FIG. 2 is a depiction of an embodiment of an antenna of a telemetry extension cable of the disclosure.

FIG. 2 shows a depiction of another embodiment of an RF antenna 30 that is useful in certain embodiments of telemetry extension cables. RF Antenna 30 having bottom planar side 26 facing upwards comprises coil conductor 18 within a polymer coating 22 with a cable 12 attached to the substantially disc shaped RF antenna 30. In this embodiment, RF antenna 30 further comprises a magnet 32. The magnet 32 is useful in activating telemetry electronics within an implanted medical device when the RF antenna 30 containing the magnet 32 is placed on a patient over or in close proximity to the implanted medical device. Magnet 32 is suitably positioned within the hole 34 of the substantially planar disc shaped antenna 30 so as to not interfere with telemetry communications. The magnet 32 may be an integral part of the RF antenna for example, through a molding process. Alternatively, the magnet may be attached to a flap that is attached to a part of the RF antenna (not shown) which may be folded out of the way of the coiled conductor after activating the telemetry within the implanted medical device.

Useful conductive materials for use in the cable 12 and in the coiled conductor in the antenna include metal wire, metal cables, metal meshes, and the like. Useful metals include copper, aluminum, platinum, gold, silver, and alloys of any of them. Useful polymers that can be used as coating materials on the cable and antennas include polyamides, polyimides, polyethers, PEEK, silicones, and polyurethanes. Useful magnets include ceramic and rare-earth magnets such as those that contain neodymium. The cable typically contains four conductors with a pair of conductors present for redundancy. The cable may also contain a cable shield.

Figure 3:
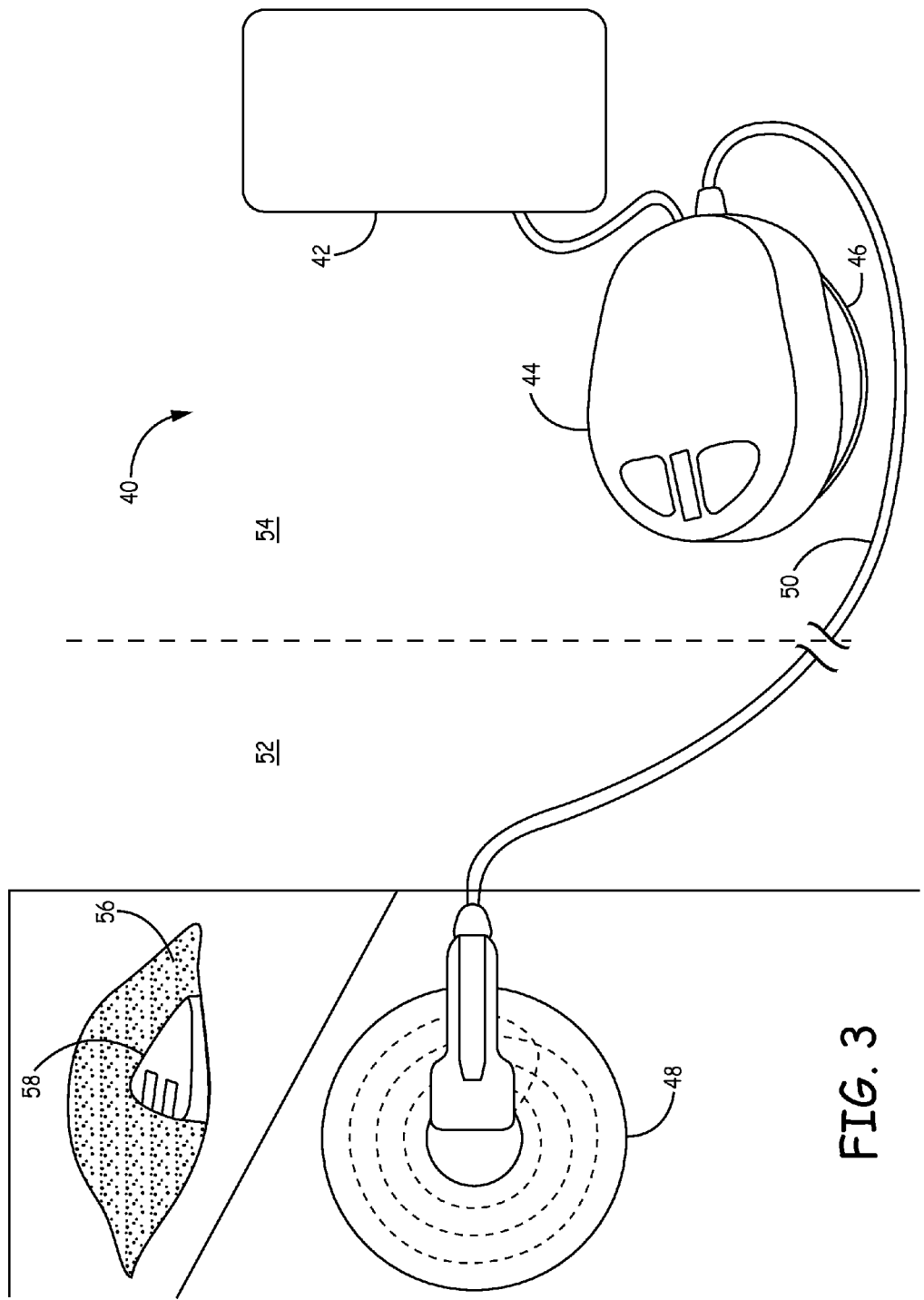
FIG. 3 is a depiction of an embodiment of a telemetry extension cable of the disclosure in use.

FIG. 3 is a depiction of a system for connecting an external medical device to an implantable medical device in use. System 40 includes an external medical device 42 having a telemetry head 44 connected to the external medical device. The telemetry head 44 is placed over a first RF antenna 46. First RF antenna is connected to second RF antenna 48 via conductive cable 50. In this depiction, a portion of cable 50 and the second RF antenna are within a sterile area or zone 52 and a portion of the cable and the first RF antenna are within a non-sterile area or zone 54. Within the sterile zone, the first RF antenna 48 is positioned in close proximity to the incision or "pocket" 56 in which the implantable medical device 58 is within. In this manner, a physician could test the implantable medical device before closing the incision, without having to having to sterilize a telemetry head and possibly an external medical device, for example, a programmer. Additionally, it is contemplated that the telemetry extension cables could be made of materials durable enough to withstand a sterilization process, yet be inexpensive enough to be considered disposable.

Generally, the RF antennas of the telemetry extension cables can be made by known methods such as compression molding. The cable can be made by extrusion or other conductor or wire coating techniques.

The telemetry extension cables described in this disclosure can be used to connect legacy implantable medical devices via RF telemetry, with an external medical device without having to sterilize the external medical device. Additionally, the telemetry cables of the disclosure can further simplify connecting an implantable medical device within a sterile zone with a non-sterile external medical device, such as a programmer or monitor, by allowing the sterile portion of the telemetry extension cable to be disposable, that is, disposed of after a single use.

One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A telemetry extension cable comprising:
    a cable having a length and comprising a four active conductors and two redundant conductors;
    a first RF antenna attached at one end of the cable, the first RF antennae in the form of a substantially planar disc; and
    a second RF antenna attached at a second end of the cable, the second RF antennae in the form of a substantially planar disc, at least one of the first or second antennas configured to transmit and receive RF signals to and from an implantable medical device, wherein each of the first and second RF antennae comprises an array of planar, coiled conductors.

2. The telemetry extension cable of claim 1 wherein one of the first or the second RF antennae further comprises a magnet.

3. The telemetry extension cable of claim 1 wherein the cable and each of the first and second antennae further comprise a coating of a polymer material capable of being sterilized.

4. A system for connecting an external medical device to an implantable medical device comprising:
    an external medical device having a telemetry head connected to the external medical device; and
    a telemetry extension cable having first and second RF antennae at each end of the telemetry extension cable, the first RF antenna configured to be placed under the telemetry head, the second RF antenna configured to transmit and receive RF signals to and from an implantable medical device, each of the first and second RF antennae being in the form of a substantially planar disc and comprising an array of planar, coiled conductors.

5. A kit comprising:
    a cable having a first portion with a first length and a second portion with a second length, the first portion of the cable having a first RF antenna in the form of a substantially planar disc and comprising an array of planar, coiled conductors at an end,
    the second portion of the cable having a second RF antenna in the form of a substantially planar disc and comprising an array of planar, coiled conductors on an end,
    at least one of the first or second cable portions is sterile.

6. The kit of claim 5 wherein the first or second sterile cable portion is packaged within sterile packaging.

7. The kit of claim 5 wherein at least the first or second sterile cable portion is disposable.

* * * * *